United States Patent
Lee et al.

(10) Patent No.: US 9,295,709 B2
(45) Date of Patent: Mar. 29, 2016

(54) PHARMACEUTICAL COMPOSITION COMPRISING MICRORNA-30B, MICRORNA-133A, OR MICRORNA-202-5P INHIBITOR FOR INHIBITING CANCER

(71) Applicant: KYUNGPOOK NATIONAL UNIVERSITY INDUSTRY-ACADEMIC COOPERATION FOUNDATION, Daegu (KR)

(72) Inventors: You-Mie Lee, Daegu (KR); Su Young Oh, Daegu (KR)

(73) Assignee: Kyungpook National University Industry-Academic Cooperation Foundation (KR)

( * ) Notice: Subject to any disclaimer, the term of this patent is extended or adjusted under 35 U.S.C. 154(b) by 0 days.

(21) Appl. No.: 14/625,137

(22) Filed: Feb. 18, 2015

(65) Prior Publication Data
US 2015/0238564 A1 Aug. 27, 2015

(30) Foreign Application Priority Data

Feb. 21, 2014 (KR) .......................... 10-2014-0020682

(51) Int. Cl.
| | | |
|---|---|---|
| *A61K 48/00* | (2006.01) | |
| *C12N 15/11* | (2006.01) | |
| *A61K 38/16* | (2006.01) | |
| *C12N 15/113* | (2010.01) | |

(52) U.S. Cl.
CPC .............. *A61K 38/16* (2013.01); *C12N 15/113* (2013.01); *C12N 2310/113* (2013.01); *C12N 2310/141* (2013.01); *C12N 2310/3181* (2013.01)

(58) Field of Classification Search
USPC ........................................... 514/44; 536/24.5
See application file for complete search history.

(56) References Cited

FOREIGN PATENT DOCUMENTS

WO   WO 2008061537 A2 * 11/2007

OTHER PUBLICATIONS

Du et al., A high-throughput screen identifies miRNA inhibitors regulating lung cancer cell survival and response to paclitaxel. RNA Biology, 2013, 10(11):1700-1713.
Chiba et al., MicroRNAs and Their Therapeutic Potential for Human Diseases: MiR-133a and Bronchial Smooth Muscle Hyperresponsiveness in Asthma. J Pharmacol Sci, 2010, 114:264-268.

* cited by examiner

*Primary Examiner* — Terra C Gibbs
(74) *Attorney, Agent, or Firm* — Riverside Law LLP

(57) ABSTRACT

Provided is an anticancer composition, and particularly, a pharmaceutical composition for inhibiting cancer, which includes a microRNA-30b, microRNA-133a, or microRNA-202-5p inhibitor as an active ingredient. The pharmaceutical composition may suppress microRNA-30b, microRNA-133a, or microRNA-202-5p, thereby inhibiting proliferation of cancer cells, and eventually, is expected to be useful for cancer treatment.

6 Claims, 7 Drawing Sheets

FIG. 2

(SEQ ID NO: 4)
(Transcript) 5' ACAGGUUAUAAACUUA                              C 3'
                                    AGU    GGA  GUUUAC
                                    | | |  | | | | | | | | |
                                    UCA    CCU  CAAAUG
(miRNA)     3'                   C     CAU    A        U 5'
                                    (SEQ ID NO: 5)

FIG. 4

| Score | Expect | Identities | Gaps | Strand |
|---|---|---|---|---|
| 14.4 bits(7) | 0.63 | 7/7(100%) | 0/7(0%) | Plus/Minus |

Query  8   CCTTCA  14
           ||||||
Sbjct  786 CCTTCA  780

PHARMACEUTICAL COMPOSITION COMPRISING MICRORNA-30B, MICRORNA-133A, OR MICRORNA-202-5P INHIBITOR FOR INHIBITING CANCER

STATEMENT REGARDING GOVERNMENT RIGHTS

This invention was made with government supports of the Republic of Korea under Contract Nos. 1220130 and 2012-007369 awarded by Korean Ministry of Health and Welfare, and the Ministry of Education, respectively. The government has certain rights in the invention.

CROSS-REFERENCE TO RELATED APPLICATION

This application claims priority to and the benefit of Korean Patent Application No. 2014-0020682, filed on Feb. 21, 2014, the disclosure of which is incorporated herein by reference in its entirety.

BACKGROUND

1. Field of the Invention

The present invention relates to an anticancer composition, and more particularly, to a pharmaceutical composition for inhibiting cancer, which includes a microRNA-30b, microRNA-133a, or microRNA-202-5p inhibitor as an active ingredient.

2. Discussion of Related Art

Cancer is a disease becoming the most major cause of death over the world, exceeding the death due to heart diseases and cerebrovascular diseases. According to the development of economy and changes in a lifestyle and an eating pattern, a type of occurring disease may be changed and cancer incidence increases, resulting in approximately 7,600,000 persons dying of cancer and 12,660,000 new cancer patients occurring in 2008. Therefore, there is a trend of consistent increases in the occurrence of cancer and a death rate caused by cancer. As the society is developed and the population is aging, it is expected that a burden of cancer occurrence will further increase and a cancer incidence in young people gradually increases due to a genetic cause and stress, and therefore the importance of preventing and treating cancer is further magnified. However, since there is no innovative cancer treating method such as development of an anticancer agent having an excellent effect and no side effect, the development of the innovative cancer treating method is urgently needed.

For example, a method of inhibiting tumor and cancer cell proliferation by limiting supply of oxygen and nutrients is actively being developed. To this end, expression of factors involved in glucose metabolism and angiogenesis among genes of tumors and cancer cells expressed in a hypoxia state and an adaptive mechanism to a surrounding microenvironment are important to understand growth and proliferation of tumors and cancer cells.

MicroRNAs (miRNAs) are small non-coding RNAs inhibiting expression of a gene in post-transcriptional regulation. MicroRNA has a hair pin structure formed of averagely 18 to 25 nucleotides. MicroRNA complementarily binds to a 3' UTR region of a target gene sequence, thereby inhibiting degradation of mRNA or translation to a protein, and approximately 5000 or more human genes are defined as targets of microRNA. As a result, depending on which target gene is regulated, the functions of microRNA in a living organism are diversified into cell differentiation and proliferation, genesis and metabolic regulation, angiogenesis, cell death, etc., and the importance of the role of microRNA is further emphasized and thus the research on microRNA is actively progressing.

Modified microRNA expression patterns are reported in various types of cancer, and known to be involved in regulation of cancer promoters or cancer suppressors. In addition, it has also been found that microRNA regulates angiogenesis, and a new therapeutic method for inhibiting a vascular disease and cancer through such a mechanism is being proposed. There is an urgent need for developing an anticancer drug for preventing formation of cancer cells in an early stage through a mechanism of regulating expression of cancer-relating genes by microRNA and suppressing angiogenesis induced by cancer.

Meanwhile, PTEN (phosphatase and tensin homologue) is known as a representative tumor suppressor serving as a phosphatase with respect to a cell membrane phospholipid, that is, phosphatidylinositol (3,4,5)-trisphosphate (PIP3). It is known that when PTEN is lost or modified, a PIP3 pathway is excessively activated and thus occurrence of various cancers such as brain cancer, breast cancer, glioma, prostate cancer, endometrial cancer, etc. are stimulated. The loss of PTEN reduces sensitivity to Fas, thereby inducing an autoimmune disease, and causes a genetic disease such as Cowden's disease or Lhermitte-Duclos disease, in addition to the occurrence of tumor. It shows that PTEN can play an important role in brain development as well as inhibition of cancer.

However, a molecular-level action mechanism of PTEN and a target thereof have not been clearly known so far. Accordingly, identification of the action mechanism of PTEN and development of a new drug for specifically regulating the PTEN mechanism are very important in development of an anticancer drug.

SUMMARY OF THE INVENTION

Therefore, the inventors found specific microRNA associated with cancer suppression in a hypoxia environment without a side effect and have studied to find an effective composition for cancer treatment, and thus confirmed a recovery effect of inhibiting PTEN expression, in which PTEN is reduced in a hypoxia environment in liver cancer cells when microRNA-30b, microRNA-133a, or microRNA-202-5p is suppressed, resulting in completing the present invention.

The present invention is directed to providing a pharmaceutical composition for inhibiting cancer, which includes a microRNA-30b, microRNA-133a, or microRNA-202-5p inhibitor as an active ingredient.

However, technical objects to be achieved in the present invention are not limited to the above-described objects, and others that are not described herein will be clearly understood to one of ordinary skill in the art from the following descriptions.

In one aspect of the present invention, a pharmaceutical composition for inhibiting cancer, which includes an inhibitor with respect to at least one microRNA selected from the group consisting of microRNA-30b, microRNA-133a, and microRNA-202-5p as an active ingredient, is provided.

In another aspect of the present invention, a method of preventing or treating cancer including administering a pharmaceutically-effective dose of the inhibitor to an individual is provided.

In still another aspect of the present invention, a method of using the inhibitor to prevent or treat cancer is provided.

In one embodiment of the present invention, the microRNA-30b is composed of a base sequence of SEQ. ID. NO: 1.

In another embodiment of the present invention, the microRNA-133a is composed of a base sequence of SEQ. ID. NO: 2.

In still another embodiment of the present invention, the microRNA-202-5p is composed of a base sequence of SEQ. ID. NO: 3.

In yet another embodiment of the present invention, the inhibitor is a peptide nucleic acid (PNA), a small interfering RNA (siRNA), an aptamer, or an antisense RNA complementarily binding to microRNA.

In yet another embodiment of the present invention, the composition exhibits an anticancer effect due to recovery of PTEN expression suppressed in a hypoxia state.

In yet another embodiment of the present invention, the cancer is liver cancer.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which:

FIG. 2 is a diagram of a binding site between microRNA-30b and 3'-UTR of PTEN;

FIG. 4 is a diagram of a binding site between microRNA-133a and 3'-UTR of PTEN;

DETAILED DESCRIPTION OF EXEMPLARY EMBODIMENTS

The present invention provides a pharmaceutical composition for inhibiting cancer, which includes a microRNA-30b, microRNA-133a, or microRNA-202-5p inhibitor as an active ingredient.

Since it is known that expression of a tumor suppressor, that is, PTEN, is reduced in a hypoxia state, the inventors confirmed whether PTEN expression was regulated by obtaining a protein after liver cancer cell lines (HepG2) were treated with a miRNA inhibitor to investigate miRNA regulating the PTEN expression in a hypoxia state. As a result, when inhibitors for three kinds of miRNAs (miR-30b, miR-133a, miR-202-5p) were treated, it was confirmed that PTEN expression was increased in every case (refer to FIG. 1).

In addition, the inventors expected that when mRNA of PTEN was degraded or suppressed by binding microRNA-30b, microRNA-133a, or microRNA-202-5p to a 3'-UTR site of PTEN, the expression of a PTEN protein would be inhibited, and to this end, investigated whether miRNAs bound to the 3'-UTR site of PTEN using a miRNA target prediction program (DIANA, microrna) and sequence alignment (NCBI). As a result, binding of miR-30b and miR-202-5p was confirmed using the miRNA target prediction program (DIANA, microrna), and miR-133a binding was confirmed using the sequence alignment (NCBI) (refer to FIGS. 2 to 4).

Figure 5:
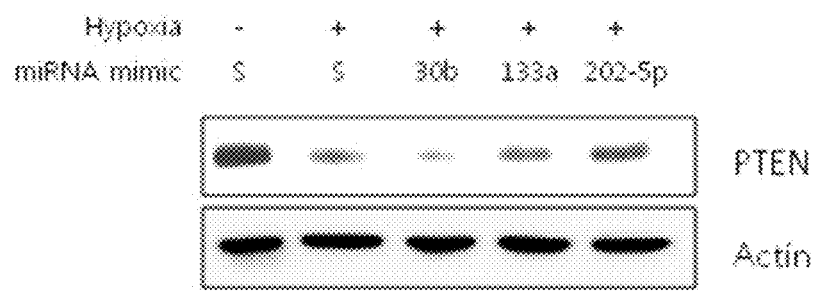
FIG. 5 shows a result obtained by confirming changes in expression of a PTEN protein inhibited in a hypoxia state by mimics of microRNA-30b, microRNA-133a, and microRNA-202-5p, and S indicates a scramble.
Figure 7:
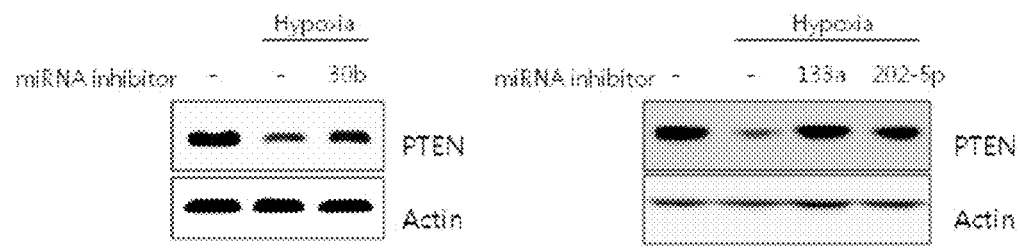
FIG. 7 shows a result obtained by confirming recovery of expression of a PTEN protein inhibited in a hypoxia state by microRNA-30b, microRNA-133a, and microRNA-202-5p inhibitors.

Based on such results, the inventors conducted western blotting after the inhibitor and a homologue thereof were applied to liver cancer cell lines (HepG2) and a protein was extracted to confirm how the microRNA-30b, microRNA-133a, or microRNA-202-5p inhibitor and a homologue thereof affected reduced PTEN expression in cancer cells in a hypoxia state (refer to FIGS. 5 and 7).

As a result, it was seen that the inhibitor increases expression of PTEN, which is a tumor suppressor, and thus is used as an effective therapeutic agent to prevent or treat cancer.

Accordingly, the inventors found that the microRNA-30b, microRNA-133a, and microRNA-202-5p serve to stimulate proliferation of a tumor tissue. Eventually, the results show that cancer cell metastasis and proliferation can be inhibited by inhibiting the microRNA-30b, microRNA-133a, and microRNA-202-5p, and therefore the microRNA-30b, microRNA-133a, and microRNA-202-5p can be effectively used to treat cancer.

Mature sequences of the microRNA-30b, microRNA-133a, and microRNA-202-5p of the present invention are shown in Table 1.

TABLE 1

| Gene | Sequence No. | Sequence (5' -> 3') |
| --- | --- | --- |
| microRNA-30b | SEQ. ID. NO: 1 | UGUAAACAUCCUACACUCAGCU |
| microRNA-133a | SEQ. ID. NO: 2 | UUUGGUCCCCUUCAACCAGCUG |
| microRNA-202-5p | SEQ. ID. NO: 3 | UUCCUAUGCAUAUACUUCUUUG |

In the present invention, the term "inhibitor" is a substance complementarily binding to the microRNA-30b, microRNA-133a, and microRNA-202-5p, and may be selected from the group consisting of a peptide nucleic acid (PNA), small interfering RNA (siRNA), an aptamer, and an antisense RNA. However, the inhibitor may be any substance inhibiting expression of miRNA, and thus the present invention is not limited thereto.

The term "homologue" used herein may be, but is not limited to, a double-stranded RNA oligonucleotide exhibiting the same activity as an endogenous microRNA.

The term "anticancer" used herein refers to all actions relating to prevention and treatment of cancer, which includes an action of inhibiting proliferation of cancer cells or killing cancer cells, and inhibiting or preventing metastasis of cancer cells.

The term "hypoxia state" used herein refers to state of decreasing oxygen in cells and tissues below a physiological level, for example, an optimal level.

The pharmaceutical composition of the present invention may include a pharmaceutically available carrier. The pharmaceutically available carrier may be, but is not limited to, saline, polyethyleneglycol, ethanol, vegetable oil, or isopropyl myristate.

In addition, the present invention provides a method of treating cancer by administering a pharmaceutically effective dose of an anticancer composition including a microRNA-30b, microRNA-133a, or microRNA-202-5p inhibitor to an individual. The "individual" used herein means a subject needing to be treated, and more specifically, human or non-human primates, and mammals including mice, rats, dogs, cats, horses, and cows. In addition, the "pharmaceutically effective dose" used herein may be controlled in various ranges according to a patient's body weight, age, health condition, diet, administration time, administration method, excretion rate, and severity of a disease, which are clearly understood to one of ordinary skill in the art.

An exemplary administration dose of the pharmaceutical composition of the present invention may be suitably determined by one of ordinary skill in the art according to a condition and body weight of a patient, severity of a disease, drug type, administration route, and duration. However, the composition may be administered at a dose of 0.001 to 100 mg/kg, and preferably, 0.01 to 30 mg/kg. The administration may be performed once or several times a day. The microRNA-30b, microRNA-133a, or microRNA-202-5p inhibitor of the present invention may be present at 0.0001 to 10 wt %, and preferably 0.001 to 1 wt % with respect to a total weight of the composition.

The pharmaceutical composition may be administered by various routes to mammals such as rats, mice, livestock, humans, etc. There is no limit to administration methods, and the composition may be administered by an oral, rectal, intravenous, intramuscular, subcutaneous, endometrial, or intracerebroventricular injection.

Hereinafter, exemplary examples will be provided to help in understanding the present invention. However, the following examples are merely provided to more easily understand the present invention, not to limit the scope of the present invention.

EXAMPLES

Example 1

Test Methods 1-1. Cell Culture and Hypoxia Treatment

Liver cancer cell lines (HepG2) were added to a DMEM medium containing 10% fetal bovine serum (FBS) and 1% penicillin streptomycin, and cultured in a 37° C. constant temperature incubator with 5% carbon dioxide. When cells were sufficiently grown, the cells were incubated in a 10 cm² Petri dish for extraction of RNA (including microRNA) and separation of proteins. When separated into two culture containers, attached cells were detached from a culture container using Trypsin-EDTA, centrifuged at 1000 rpm for 5 minutes, and transferred to a new culture container by the same method as used for the attached cells. When maintained in a hypoxia state, the cells were incubated in an incubator in which 1% $O_2$ concentration was maintained for 24 hours.

1-2. Transfection of miRNA Mimic

A mixture prepared by mixing a Hiperfect reagent (Qiagene), an miRNA mimic (Bioneer), and control miRNA (Bioneer) each at a concentration of 5 nM at room temperature for 15 minutes was transfected to the liver cancer cell lines (HepG2) incubated in Example 1-1. After 24 hours, the cell lines were incubated one more day in an incubator in a hypoxia state.

1-3. Transfection of miRNA Inhibitor

A mixture prepared by mixing a Hiperfect reagent (Qiagene) and 1 μM of an miRNA inhibitor (Panagene) at room temperature for 15 minutes was transfected to the liver cancer cell lines (HepG2) incubated in Example 1-1. After 24 hours, the cell lines were incubated one more day in an incubator in a hypoxia state.

1-4. Separation of Proteins

To separate a protein from a cell, a lysis buffer (containing 25 mM of Tris, 1% (wt/vol) of Nonidet P-40, 0.25% of sodium deoxycholate, 150 mM of NaCl, 1 mM of EGTA, 1 mM of PMSF, 1 μg of aprotinin, leupeptin, pepstatin, 1 mM of $Na_3VO_4$, and 1 mM of NaF) was added to the liver cancer cell lines (HepG2) washed with PBS, and maintained on ice for 30 minutes. The resulting mixture was centrifuged at 15,000 rpm and 4° C. for 20 minutes, and a supernatant was taken, quantified, and then stored at −70° C. for the next use.

1-5. Western Blot

According to each condition, cell extracts were obtained to perform an SDS-containing polyacrylamide gel electrophoresis (SDS-PAGE). After the electrophoresis, transfer was performed onto a nitrocellulose filter at 90 V for 1 hour, and blocking was performed using 5% non-fat milk-containing TBS. Afterward, the filter was reacted with a primary antibody and a secondary antibody, and washed with 0.1% tween-20-containing TBS, and then detection was performed using an ECL detection kit. Here, the used primary antibody was diluted in a concentration of 1:1,000, and the secondary antibody was diluted in a concentration of 1:5,000.

1-6. RT-PCR

To prevent RNA degradation caused by an RNase, which occurs easily, test materials and equipment, and a surface of a work station were sufficiently wiped with ethanol. Total RNAs were separated using Trizol (BD bioscience). A concentration of the separated RNA from the liver cancer cell lines (HepG2) was confirmed, reverse-transcription of 1 μg of RNA was performed with 150 ng of a random primer, 4 mM of dNTP, 1 μl of RNasin, and 1 μl of M-MLV RTase at 37° C. for 1 hour. PCR was performed on cDNA obtained by the reverse transcription. 20 μl of a reaction solution was used for PCR for 30 to 35 cycles using a PCR machine, thereby obtaining a PCR product. The product was analyzed by electrophoresis.

1-7. Prediction Program for microRNA-Target Gene Binding Sites

To predict binding sites between microRNA-30b, microRNA-133a and microRNA-202-5p, and a target gene PTEN, a microRNA target prediction program (DIANA, microrna) and a sequence alignment program (NCBI) were used.

Example 2

Screening of miRNA Targeting PTEN Gene

To screen miRNA regulating PTEN expression in a hypoxia state, according to Examples 1-1 to 1-5, HepG2 cells were treated with a PNAs™ miRNA inhibitor (PANAGENE) for 24 hours, thereby obtaining a protein, and western blotting was performed to confirm whether PTEN expression was regulated.

Figure 1:
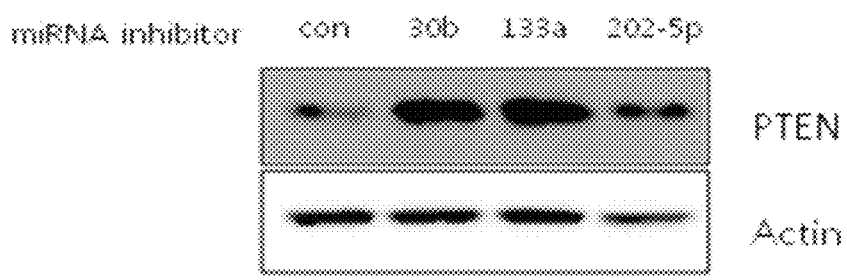
FIG. 1 shows a result obtained by confirming changes in a PTEN protein expression level by microRNA-30b, microRNA-133a, and microRNA-202-5p inhibitors, and con indicates a control.

Consequently, as shown in FIG. 1, it was confirmed that PTEN expression increased in all cases that three types of miRNA (miR-30b, miR-133a, and miR-202-5p) inhibitors were treated.

Example 3

Detection of Binding of miRNA (miR-30b, miR-133a, miR-202-5p) with PTEN

According to Example 2, the inventors predicted that PTEN decreased in expression in cancer cells under a hypoxia condition would serve as a target gene of miRNA (miR-30b, miR-133a, or miR-202-5p), and the miRNA would bind to the 3'-UTR site of PTEN, thereby degrading or inhibiting mRNA of PTEN, and therefore the expression of the PTEN protein would be inhibited.

Accordingly, to confirm this, the binding of the miRNA to the 3'-UTR site of PTEN was detected using a miRNA target prediction program (DIANA, microrna) and a sequence alignment program (NCBI).

Figure 3:
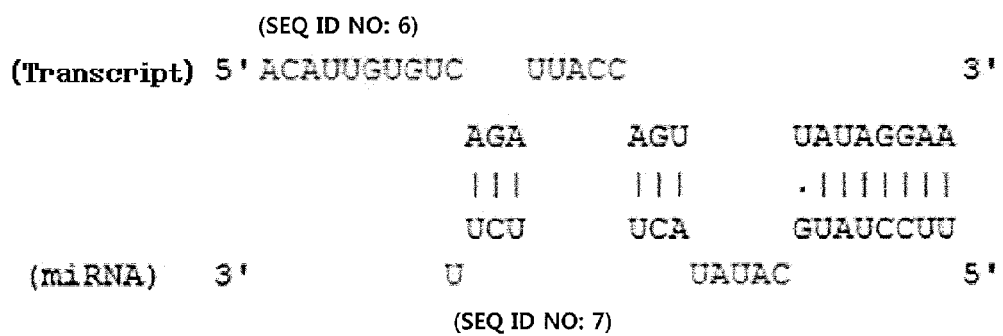
FIG. 3 is a diagram of a binding site between microRNA-202-5p and 3'-UTR of PTEN.

Consequently, as shown in FIGS. 2 to 4, it was confirmed that the binding site between 3'-UTR of mRNA of PTEN and miRNA (miR-30b, miR-133a, miR-202-5p) was conserved.

Example 4

Regulation of PTEN Expression by miRNA

To confirm an effect of miR-30b, miR-133a, and miR-202-5p on PTEN inhibited in expression due to hypoxia, HepG2 cells were treated with a mimic for each miRNA for 24 hours and incubated for 24 hours in a hypoxia state, and then an expression level of the PTEN protein was detected by western blotting. Here, as the miRNA mimic, an AccuTarget™ human miRNA mimic (BIONEER) was used.

Consequently, as shown in FIG. 5, it was confirmed that expression of the PTEN protein decreased by hypoxia treatment was further decreased or similar when the miRNA-30b, miR-133a, or miR-202-5p mimic was treated.

Figure 6:
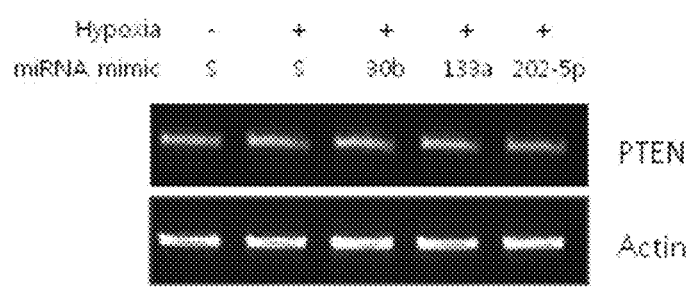
FIG. 6 shows a result obtained by confirming changes in expression of a PTEN mRNA inhibited in a hypoxia state by mimics of microRNA-30b, microRNA-133a, and microRNA-202-5p, and S indicates a scramble.

In addition, as shown in FIG. 6, HepG2 cells were treated with an miRNA mimic and total RNA was extracted to synthesize cDNA by reverse transcription. As a result of PCR, it was shown that there was no difference in change in mRNA of PTEN.

Example 5

Recovery of PTEN Inhibition by miRNA Inhibitor

To confirm an effect of miR-30b, miR-133a, and miR-202-5p on PTEN inhibited in expression due to hypoxia, HepG2 cells were treated with an inhibitor with respect to each miRNA for 24 hours and incubated for 24 hours in a hypoxia state, and then an expression level of the PTEN protein was detected by western blotting. Here, as the miRNA inhibitor, a PNAs™ miRNA inhibitor (PANAGENE) was used.

Consequently, as shown in FIG. 7, it was confirmed that expression of a PTEN protein reduced by a hypoxia treatment was recovered when an miRNA-30b, miR-133a, or miR-202-5p inhibitor was treated.

A pharmaceutical composition of the present invention can suppress microRNA-30b, microRNA-133a, or microRNA-202-5p, thereby inhibiting proliferation of cancer cells, and eventually, is expected to be useful for cancer treatment.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method for treating cancer by recovering phosphatase and tensin homologue (PTEN) expression inhibited in a hypoxia state in a subject in need thereof, comprising administering a pharmaceutically effective amount of an inhibitor to at least one microRNA selected from the group consisting of microRNA-30b, microRNA-133a, and microRNA-202-5p to the subject.

2. The method of claim 1, wherein the microRNA-30b is represented by a base sequence of SEQ. ID. NO: 1.

3. The method of claim 1, wherein the microRNA-133a is represented by a base sequence of SEQ. ID. NO: 2.

4. The method of claim 1, wherein the microRNA-202-5p is represented by a base sequence of SEQ. ID. NO: 3.

5. The method of claim 1, wherein the inhibitor is PNA (peptide nucleic acid), siRNA (small interfering RNA), an aptamer, or an antisense RNA complementarily binding to the microRNA.

6. The method of claim 1, wherein the cancer is liver cancer.

* * * * *

SEQUENCE LISTING

```
<160> NUMBER OF SEQ ID NOS: 7

<210> SEQ ID NO 1
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 1
uguaaacauc cuacacucag cu                                              22

<210> SEQ ID NO 2
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 2
uuuggucccc uucaaccagc ug                                              22

<210> SEQ ID NO 3
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 3
```

```
uuccuaugca uauacuucuu ug                                              22

<210> SEQ ID NO 4
<211> LENGTH: 29
<212> TYPE: RNA
<213> ORGANISM: Artificial Sequence
<220> FEATURE:
<223> OTHER INFORMATION: Chemically Synthesized

<400> SEQUENCE: 4
acagguuaua aacuuaagug gaguuuacc                                       29

<210> SEQ ID NO 5
<211> LENGTH: 18
<212> TYPE: RNA
<213> ORGANISM: Artificial Sequence
<220> FEATURE:
<223> OTHER INFORMATION: Chemically Synthesized

<400> SEQUENCE: 5
uguaaacauc cuacacuc                                                   18

<210> SEQ ID NO 6
<211> LENGTH: 29
<212> TYPE: RNA
<213> ORGANISM: Artificial Sequence
<220> FEATURE:
<223> OTHER INFORMATION: Chemically Synthesized

<400> SEQUENCE: 6 acauguguc agauuaccag uuauaggaa                                        29

<210> SEQ ID NO 7
<211> LENGTH: 20
<212> TYPE: RNA
<213> ORGANISM: Artificial Sequence
<220> FEATURE:
<223> OTHER INFORMATION: Chemically Synthesized

<400> SEQUENCE: 7
uuccuaugca uauacuucuu                                                 20
```